United States Patent
Baiker et al.

(10) Patent No.: US 6,369,274 B1
(45) Date of Patent: Apr. 9, 2002

(54) METHOD FOR PRODUCING CYCLOHEXANEDIAMINES

(75) Inventors: Alfons Baiker, Opfikon; Tamas Mallat, Zürich, both of (CH); Achim Fischer, Gelnhausen (DE)

(73) Assignee: Lonza AG (CH)

( * ) Notice: Subject to any disclaimer, the term of this patent is extended or adjusted under 35 U.S.C. 154(b) by 0 days.

(21) Appl. No.: 09/831,353

(22) PCT Filed: Nov. 8, 1999

(86) PCT No.: PCT/EP99/08553

§ 371 Date: Jul. 20, 2001

§ 102(e) Date: Jul. 20, 2001

(87) PCT Pub. No.: WO00/29367

PCT Pub. Date: May 25, 2000

Related U.S. Application Data

(60) Provisional application No. 60/159,545, filed on Oct. 15, 1999.

(30) Foreign Application Priority Data

Nov. 12, 1998 (EP) ............................................. 98121482

(51) Int. Cl.$^7$ ............................................. C07C 209/00
(52) U.S. Cl. ........................ 564/447; 564/461; 564/462
(58) Field of Search ................................ 564/447, 461, 564/462

(56) References Cited

U.S. PATENT DOCUMENTS

| | | |
|---|---|---|
| 5,773,657 A | 6/1998 | Rütter et al. |
| 5,789,620 A | 8/1998 | Waldmann et al. ......... 148/273 |

OTHER PUBLICATIONS

A. Fisher et al., Journal Of Catalysis, vol. 182, No. 2, (1999), pp. 289–291.

*Primary Examiner*—Samuel Barts
(74) *Attorney, Agent, or Firm*—Fisher, Christen & Sabol

(57) ABSTRACT

1,n-cyclohexanediamines (n=2, 3, 4) of general formula (I), wherein one of the radicals $R^1$ to $R^3$ is an amino group and the two others mean hydrogen, are produced from the corresponding cyclohexanediols and ammonia in the presence of a catalyst containing cobalt, at 100° to 350° C. and 50 to 300 bar. The compounds that can be produced according to the invention are structural elements for polymers, especially polyamides, polyimides, polyurea or polyurethanes, and ligands for cytostatically effective transition metal complexes.

18 Claims, No Drawings

METHOD FOR PRODUCING CYCLOHEXANEDIAMINES

This application is a 371 application of PCT/EP99/08553, filed on Nov. 8, 1999, which has priority benefit of European Patent Application 98121482.8, filed on Nov. 12, 1998, and which has priority benefit of U.S. Provisional Application No. 60/159,545, filed on Oct. 15, 1999, which has priority benefit of European Patent Application 98121482.8, filed on Nov. 12, 1998.

The invention relates to a process for preparing 1,n-cyclohexanediamines, where n may have the values 2, 3 and 4. These compounds have the general formula

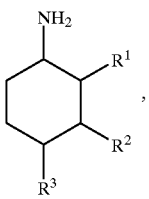
I where one of the radicals $R^1$ to $R^3$ is an amino group and the two others are hydrogen.

1,n-Cyclohexanediamines, in particular, 1,4-cyclohexanediamine ($R^3$=$NH_2$), are compounds with a variety of potential uses. Of particular interest is their use as building blocks for polymers, for example as an amino component for preparing polyamides, polyimides or polyureas, or as a starting material for preparing diisocyanates for the preparation of polyurethanes. These compounds are, furthermore, bidentate ligands which with various transition metals form complexes of which some are pharmacologically active, for example as cytostatics.

Processes known hitherto for preparing 1,n-cyclohexanediamines are based on the hydrogenation of the corresponding phenylenediamines However, these are relatively expensive, highly toxic and, in particular the para isomer, sensitive to oxidation. There are also processes for the direct hydrogenation of the corresponding nitroanilines, but these are also highly toxic.

The object of the present invention was therefore to provide a process, suitable for carrying out on an industrial scale, and starting from readily obtainable and relatively nonhazardous compounds, for preparing 1,n-cyclohexanediamines.

According to the invention, this object is achieved by the process of the invention.

It has been found that 1,n-cyclohexanediols of the general formula

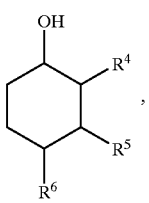
II where one of the radicals $R^4$ to $R^6$ is a hydroxyl group and the others are hydrogen, can be converted into the desired 1,n-cyclohexanediamines by reacting with ammonia in the presence of hydrogen and of a catalyst based on cobalt, if desired with addition of iron as promoter, in a single-step process at reaction pressures of from 50 to 300 bar and at temperatures of from 100 to 350° C. The proportional quantities are usefully 2–200 mol of ammonia and 0.01–20 mol of hydrogen to 1 mole of 1,n-cyclohexanediol. Preference is given to proportional quantities of 10–100 mol, in particular 40–90 mol, of ammonia and 2–10 mol of hydrogen to 1 mole of 1,n-cyclohexanediol.

The reaction pressure is preferably 100–300 bar.

Particular preference is given to pressures of 125–200 bar and to temperatures of 150–230° C.

The metal fraction of the catalyst, calculated without any support which may be present, is preferably from 90 to 100 per cent by weight.

Particular preference is given to catalysts which, in addition to the cobalt, comprise from 1 to 60 per cent by weight (based on the total metal content) of iron as promoter. The scope of the invention also includes the use of other promoters, such as rare-earth metals.

The catalysts which may be used according to the invention may, for example, be prepared by precipitating the hydroxides, oxide hydrates and/or hydroxycarbonates of the active metals at pH 5–9, washing the same, drying the same and calcining the same at 200–500° C., preferably 300–500° C., in an oxidizing atmosphere.

It is advantageous for carrying out the reaction according to the invention if there are basic and acid centres present on the catalyst surface, since adsorption and activation of the ammonia and of the aminoalcohol arising as intermediate can take place at these centres. However, strongly basic or strongly acid centres are disadvantageous, since they reduce the selectivity of the reaction and favour side reactions, such as fragmentation and oligomerization. The pH value during the precipitation affects the acid and/or basic properties of the catalyst. It is therefore essential to carry out the precipitation at a pH of from 5 to 9.

The precipitation may, for example, be brought about by adding a base to a solution of the acetates, nitrates or halides of the metal component(s). Preferred bases are ammonium carbonate and/or ammonium carbamate or ammonia.

The drying preferably takes place at temperatures of up to 150° C., if desired in vacuo.

Prior to use the catalyst is advantageously activated in a reducing atmosphere (e.g. hydrogen) at 200–400° C. The catalyst in the active form is essentially in metallic form.

The catalyst may have been applied to a support, such as silicon dioxide (e.g. kieselguhr), aluminium oxide or graphite. To this end, the precipitation may take place in the presence of the support.

The novel process is preferably carried out continuously.

The contact time (defined as the quotient calculated from weight of catalyst [g] and molar feed [mol/s] of the reaction partners in the case of continuous operation is preferably 10,000 to 100,000 g·s/mol.

In the case of continuous conduct of the reaction, the unconverted alcohol and/or the unconverted ammonia is preferably recycled. By this means it is possible to obtain a good product yield even under conditions which during a single pass give only low conversion. The ammonia may be introduced to the reactor as a gas or liquid. The reaction mixture leaving the reactor is advantageously cooled, e.g. by adiabatic expansion, and the ammonia separated off and, if desired, returned to the process.

The examples below illustrate the conduct of the novel process but are not intended to be limiting.

EXAMPLE 1

Preparation of a Co/Fe Catalyst

The salts $Co(NO_3)_2 \cdot 6H_2O$ and $Fe(NO_3)_3 \cdot 9H_2O$ are dissolved in water in a molar ratio of 20:1 and in a total concentration of 0.36 mol/l, and mixed with a 20% strength aqueous solution of commercially available "ammonium carbonate" (mixture of carbonate and carbamate) until pH 7 is achieved, whereupon cobalt and iron precipitated as hydroxycarbonates.

The precipitate was filtered off, carefully washed with water, dried in vacuo at 100° C. and calcined at 400° C. for 2 h in air. Prior to use, the resultant catalyst was activated for 4 h at 350° C. and 40 bar in hydrogen. The resultant catalyst had a BET specific surface area of 12 m²/g and an average pore diameter of 43 nm. An X-ray scattering diagram showed the cobalt to be present essentially in the β phase.

EXAMPLE 2

1,4-Cyclohexanediamine

The reaction was carried out continuously in a fixed-bed tubular reactor. The reactor was composed of a tube with an internal diameter of 13 mm and with a length of 304 mm, made from Inconel®-718. It contained 8 of the Co/Fe catalyst from Example 1. A reaction mixture made from 1,4-cyclohexanediol, ammonia and hydrogen in the reactor. The reaction temperature was 165° C., the pressure was 135 bar and the contact time was 40,000 g·s/mol. The conversion achieved was 76%. The product mixture comprised 1,4-cyclohexanediamine and 4-aminocyclohexanol, corresponding to a selectivity of 55% and 42%.

EXAMPLE 3

1, 4-Cyclohexanediamine

The procedure was described in Example 2, but the reaction temperature was 195° C. and the contact time was 20,000 g·s/mol. The conversion was 99% and the yield of 1,4-cyclohexanediamine was 65%. 6% of 4-aminocyclohexanol and 26% of other products were also found.

EXAMPLE 4

1,4-Cyclohexanediamine

The procedure was as described in Example 2, but the unreacted diol was recycled. The conversion was 95% and the yield of 1,4-cyclohexanediamine was 51%. 38% of 4-aminocyclohexanol and 5% of other products were also found.

We claim:

1. The process for preparing a 1,n-cyclohexanediamine of the formula:

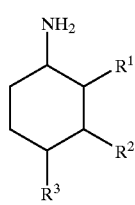

I wherein one of the radicals $R^1$ to $R^3$ is an amino group and the two others are hydrogen, comprising reacting a corresponding 1,n-cyclohexanediol of the formula:

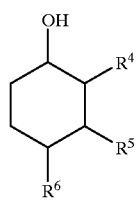

II where one of the radicals $R^4$ to $R^6$ is a hydroxyl group and the others are hydrogen, with ammonia in the presence of hydrogen and of a Co-containing catalyst at a temperature of 100° to 350° C., at a pressure of 50 to 300 bar and at a ratio of 2 to 200 mol of ammonia and 0.01 to 20 mol of hydrogen per mol of 1,n-cyclohexanediol.

2. The process according to claim 1, wherein the metal fraction of the catalyst without support is 90 to 100 percent by weight.

3. The process according to claim 2, wherein the catalyst comprises 1 to 60 percent by weight of Fe as promoter.

4. The process according to claim 3, wherein the catalyst was prepared by precipitating the corresponding hydroxides, oxide hydrates and/or basic carbonates at pH 5 to 9 followed by drying, and also calcining in an oxidizing atmosphere at 200° to 500° C.

5. The process according to claim 4, wherein the catalyst was activated at a temperature of 200° to 400° C. in a reducing atmosphere.

6. The process according to claim 5, wherein the catalyst has been applied to a support made from silicon dioxide, aluminum oxide, or graphite.

7. The process according to claim 6, wherein it is carried out continuously.

8. The process according to claim 7, wherein the contact time is 10,000 to 100,000 g·s/mol.

9. The process according to claim 8, wherein the unreacted 1,n-cyclohexanediol and/or the unreacted ammonia is recycled.

10. The process according to claim 1, wherein the catalyst comprises 1 to 60 percent by weight of Fe as promoter.

11. The process according to claim 1, wherein the catalyst was prepared by precipitating the corresponding hydroxides, oxide hydrates and/or basic carbonates at pH 5 to 9 followed by drying, and also calcining in an oxidizing atmosphere at 200° to 500° C.

12. The process according to claim 1, wherein the catalyst was activated at a temperature of 200° to 400° C. in a reducing atmosphere.

13. The process according to claim 1, wherein the catalyst has been applied to a support made from silicon dioxide, aluminum oxide, or graphite.

14. The process according to claim 1, wherein it is carried out continuously.

15. The process according to claim 14, wherein the contact time is 10,000 to 100,000 g·s/mol.

16. The process according to claim 15, wherein the unreacted 1,n-cyclohexanediol and/or the unreacted ammonia is recycled.

17. The process according to claim 14, wherein the unreacted 1,n-cyclohexanediol and/or the unreacted ammonia is recycled.

18. The process according to claim 7, wherein the unreacted 1,n-cyclohexanediol and/or the unreacted ammonia is recycled.

* * * * *